(12) United States Patent
Jansen et al.

(10) Patent No.: US 7,758,545 B2
(45) Date of Patent: Jul. 20, 2010

(54) INJECTION DEVICE

(75) Inventors: Paul Jansen, Mannheim (DE); Juergen Rasch-Menges, Schwetzingen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 307 days.

(21) Appl. No.: 11/776,370

(22) Filed: Jul. 11, 2007

(65) Prior Publication Data
US 2008/0015503 A1    Jan. 17, 2008

(30) Foreign Application Priority Data
Jul. 14, 2006    (EP)    .................................. 06014682

(51) Int. Cl.
*A61M 5/00*    (2006.01)
(52) U.S. Cl. ...................................................... 604/117
(58) Field of Classification Search ................. 604/117, 604/83
See application file for complete search history.

(56) References Cited

U.S. PATENT DOCUMENTS

| | | | |
|---|---|---|---|
| 3,656,472 A | 4/1972 | Moura et al. | |
| 4,850,973 A | 7/1989 | Jordan et al. | |
| 4,950,246 A * | 8/1990 | Muller | 604/154 |
| 5,085,642 A * | 2/1992 | Sarnoff et al. | 604/134 |
| 5,226,896 A * | 7/1993 | Harris | 604/211 |
| 5,318,584 A | 6/1994 | Lange et al. | |
| 5,536,249 A | 7/1996 | Castellano et al. | |
| 5,728,074 A * | 3/1998 | Castellano et al. | 604/207 |
| 5,876,380 A * | 3/1999 | Manganini et al. | 604/191 |
| 5,925,021 A * | 7/1999 | Castellano et al. | 604/207 |
| 6,192,891 B1 | 2/2001 | Gravel et al. | |
| 6,290,683 B1 | 9/2001 | Erez et al. | |
| 7,311,879 B2 * | 12/2007 | Hodson | 422/100 |
| 7,397,730 B2 * | 7/2008 | Skyggebjerg et al. | 368/10 |
| 2003/0050655 A1 * | 3/2003 | Roe | 606/182 |
| 2005/0137525 A1 * | 6/2005 | Wang et al. | 604/93.01 |
| 2005/0187519 A1 * | 8/2005 | Harris et al. | 604/117 |
| 2005/0234495 A1 * | 10/2005 | Schraga | 606/181 |
| 2005/0267505 A9 * | 12/2005 | Shraga | 606/182 |

(Continued)

FOREIGN PATENT DOCUMENTS

EP    0 565 970    9/1997

(Continued)

*Primary Examiner*—Nicholas D Lucchesi
*Assistant Examiner*—Diva Ranade
(74) *Attorney, Agent, or Firm*—Baker & Daniels LLP

(57) ABSTRACT

The invention refers to an injection device for the injection of a medical agent, in particular insulin, comprising: a housing, a reception compartment for a vial containing the agent to be injected, advancement mechanics for moving an injection needle that is inserted in the device in a direction of puncturing, and a pressing facility for pressing agent from a vial that is inserted in the reception compartment for the purpose of an injection process. The advancement mechanics, effects, in a first device function for an injection process, a first motion profile of an inserted injection needle, in which a resting phase follows after an advancement motion, during which resting phase the inserted injection needle for an injection process is at rest with respect to the device housing, and effects, in a second device function for obtaining a body fluid sample for diagnostic purposes, a second motion profile of an inserted injection needle, in which a returning motion follows immediately after a puncturing motion.

32 Claims, 2 Drawing Sheets

U.S. PATENT DOCUMENTS

| | | | |
|---|---|---|---|
| 2007/0118077 A1* | 5/2007 | Clarke et al. | 604/117 |
| 2007/0244412 A1* | 10/2007 | Lav et al. | 600/584 |
| 2007/0250006 A1* | 10/2007 | Court et al. | 604/117 |
| 2007/0293742 A1* | 12/2007 | Simonsen et al. | 600/316 |
| 2008/0015425 A1* | 1/2008 | Douglas et al. | 600/347 |
| 2009/0099478 A1* | 4/2009 | Cassells et al. | 600/583 |

FOREIGN PATENT DOCUMENTS

| | | |
|---|---|---|
| FR | 2 040 830 | 1/1971 |
| WO | 9302720 | 2/1993 |

* cited by examiner

INJECTION DEVICE

BACKGROUND OF THE INVENTION

1. Field of the Invention

The invention relates to an injection device for the injection of a medical agent, comprising a device housing, a reception compartment for a vial containing the agent to be injected, advancement mechanics for moving an injection needle that is inserted in the device in the direction of puncturing, and a pressing facility for pressing agent from a vial that is inserted in the reception compartment for the purpose of an injection process.

2. Description of the Prior Art

Injection devices are known and commercially available, for example, as so-called "insulin pens". They are used in particular by insulin-dependent diabetics in order to self-administer doses of insulin they need. An injection device of this type is known from U.S. Pat. No. 5,536,249, for example, which is hereby incorporated by reference.

For effective therapy, insulin-dependent diabetics need to check their glucose level multiple times daily by performing measurements on a suitable body fluid, usually blood and/or interstitial fluid. For this purpose, a suitable puncturing aid is used to generate a puncturing wound in a body part, usually a finger, and body fluid obtained from the puncturing wound is assayed by means of a test strip and a measuring device. The insulin dose to be injected is then set as a function of the glucose level thus determined and injected by means of an injection device.

A measuring device allowing the blood glucose content to be determined by means of the corresponding test strips is integrated in the injection device known from U.S. Pat. No. 5,536,249.

Despite the progress that has been made over many decades of development of puncturing aids for generating puncturing wounds for obtaining body fluid samples and of injection devices for the injection of insulin, affliction by an insulin-dependent diabetes continues to be a substantial burden for the afflicted. Multiple daily measurements and injections of insulin needed for therapy to be effective are a tedious burden that is exacerbated by the need to always carry along a puncturing device, an injection device, lancets for the puncturing device, injection needles for the injection device, insulin vials, and test strips.

SUMMARY OF THE INVENTION

Embodiments of an injection device of the present invention comprise a first device function for an injection process allowing for the advancement mechanics to effect a first motion profile of an inserted injection needle, in which a resting phase follows after an advancement motion, during which resting phase the inserted injection needle for an injection process is at rest with respect to the device housing, and effects, in a second device function for obtaining a body fluid sample for diagnostic purposes, a second motion profile of an inserted injection needle, in which a returning motion follows immediately after a puncturing motion.

An injection device according to embodiments of the invention combines the functions of a conventional puncturing aid that is used to generate a puncturing wound for obtaining a body fluid sample for diagnostic purposes, and of an injection device for the injection of a medical agent such that an insulin-dependent diabetic needs to carry along just a single device. This is equivalent to a substantial increase of the user convenience and in addition facilitates cost savings in the treatment of insulin-dependent diabetics.

In order to perform these two device functions that differ in their requirements, embodiments of the invention provide for the injection needle to be moved with different motion profiles depending on the actual device function. In the first device function that serves for the injection of a medical agent, the injection needle is advanced by means of an advancement motion and subsequently stopped such that the injection needle for an injection process is at rest with respect to the device housing. For example, the tip of the injection needle can be pushed out of a device opening during the advancement motion and the puncture can be performed manually during the resting phase.

It is also feasible for the injection needle to already be punctured by means of a drive into the skin of a patient up to a predetermined puncturing depth during the advancement motion, i.e. the advancement motion corresponds to a puncturing motion. Once the predetermined puncturing depth is reached, the injection needle is stopped and remains stuck in the body of the user during the resting phase. The actual injection process, in which the agent is pressed from the vial and into the body of the patient by the injection needle occurs during this resting phase. After completion of the injection process, the injection needle is retracted from the puncturing wound, which can be effected manually or by means of a drive. The puncturing depth for this first device function is typically approx. 2 mm to 12 mm such that the injection needle projects into the subcutaneous fatty tissue during the injection process.

If the puncture is performed manually subsequent to the advancement motion of the first device function, no drive is needed for this advancement motion since high velocities are not required for this advancement motion and the forces needed can be provided by manual means.

In the second device function for obtaining a body fluid sample, a deep puncture of this type may not be required and may cause unnecessary pain. Aside from a puncturing depth that is as small as possible, a puncturing and returning motion that is as rapid as possible may be desired for a puncture for obtaining a body fluid sample to be associated with little pain. For this reason, a rapid returning motion follows immediately after the puncturing motion in the second device function. This means that, during a segment of the motion that includes the reversal point of the motion, the injection needle is continuously exposed to a force generated by a drive that effects an acceleration in the direction of the returning motion. At the beginning of the segment of motion, the acceleration effected by the drive first effects a decrease of the velocity of advancement of the puncturing motion until the reversal point of the motion is reached. Once the reversal point is reached, i.e. at the set puncturing depth, the acceleration effects an increasingly more rapid returning motion. The drive required for the second device function is part of the advancement mechanics and can also be utilized for the first device function, if the advancement motion of the first device function is utilized to generate a puncture.

BRIEF DESCRIPTION OF THE DRAWINGS

Further details are illustrated in the following by means of exemplary embodiments and referring to the appended drawings. Equal and corresponding components are identified therein by identical reference numbers. The features illustrated in the following can be made the object of claims individually or in combination. In the figures:

DETAILED DESCRIPTION OF EMBODIMENTS OF THE INVENTION

Figure 1:
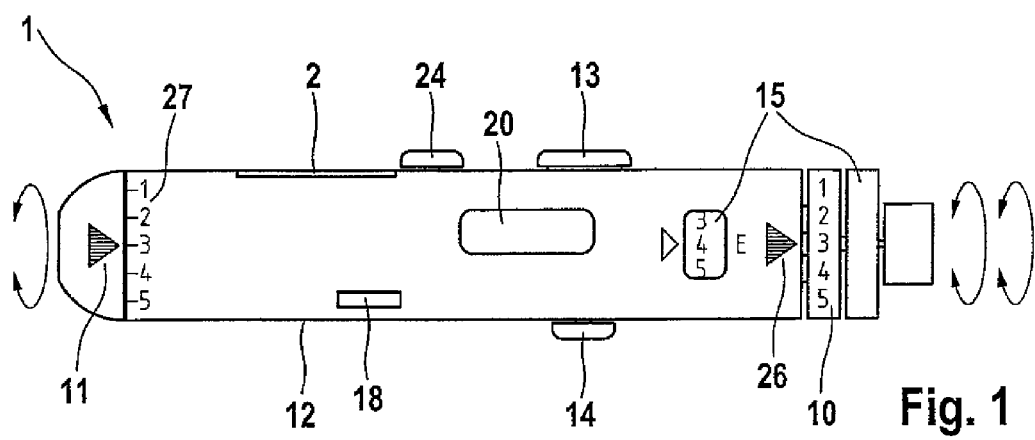
FIG. 1 shows a side view of an exemplary embodiment of an injection device according to the invention.
Figure 2:
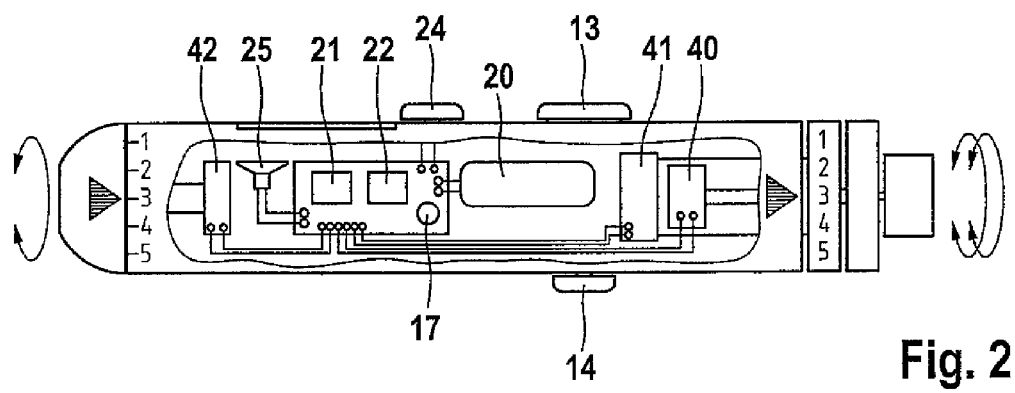
FIG. 2 shows the exemplary embodiment shown in FIG. 1 with the housing exposed.
Figure 3:
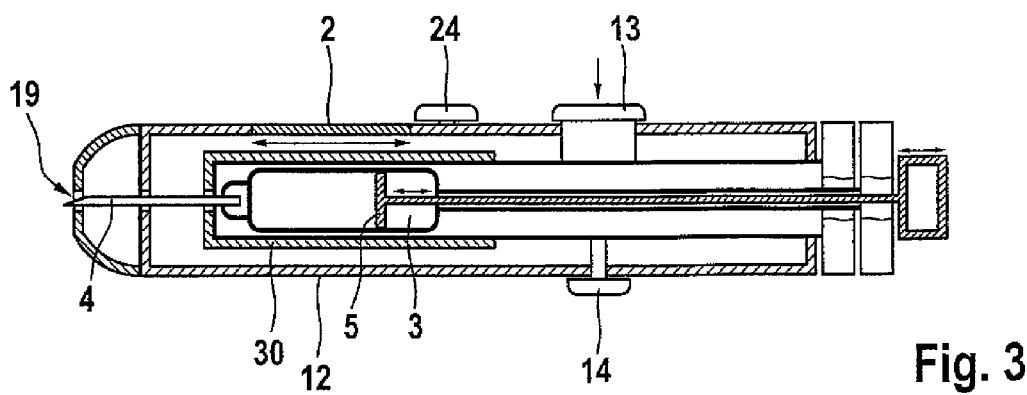
FIG. 3 shows a cross-section showing a simplified view of the exemplary embodiment shown in FIG. 1.

An exemplary embodiment of an injection device 1 for the injection of insulin shown in FIGS. 1 to 3 comprises, according to conventional design, a reception compartment 2 for an insulin vial 3, advancement mechanics having a drive for moving an exchangeable injection needle 4 that is inserted in the device for a puncturing motion for generating a puncturing wound in the skin of a user, and a pressing facility 5 for pressing-out insulin from an insulin vial 3 that has been inserted into the reception compartment for an injection process. It should be noted that in addition to a first device function that serves for the injection of insulin, it has a second device function that serves for generating a puncturing wound for obtaining a body fluid sample for diagnostic purposes. In both device functions, the drive effects a puncturing motion of an injection needle 4 that is inserted in the device 1 in order to generate a puncturing wound in the skin of a user.

In the first device function, the drive effects a first motion profile of the inserted injection needle 4, in which a resting phase, during which the inserted injection needle 4 for an injection process is at rest with respect to the device housing 12, follows after an advancement motion. The advancement motion is used to push a tip of an injection needle 4 that is inserted in the device from a device opening 19. The injection needle that has thus been advanced can be used during the resting phase to manually puncture body tissue. The puncture may occur automatically during the advancement motion and for the injection needle 4 to remain in the puncturing wound thus generated during the subsequent resting phase. The duration of the resting phase depends, among other factors, on the quantity of insulin to be injected and usually is several fractions of a second or few seconds. The puncturing depth to which the injection needle 4 is punctured into the skin of a patient in the first device function typically is between about 2 mm to about 12 mm such that the injection needle 4 projects into subcutaneous fatty tissue during the injection process.

In the second device function, the injection needle 4 is used to generate a puncturing wound for obtaining a body fluid sample for diagnostic purposes. The body fluid that is obtained from a puncturing wound generated using the second device function usually is blood and/or interstitial fluid. A body fluid sample of this type allows the glucose content to be determined and therefore allows the needed insulin dose to be determined. The drive effects a second motion profile of the inserted injection needle 4 in the second device function, in which the second motion profile is a returning motion that follows directly after a puncturing motion.

The injection device 1 comprises a setting facility 10, 11 for setting a first puncturing depth for the first motion profile for an injection process, and a second puncturing depth for the second motion profile for obtaining a body fluid sample for diagnostic purposes. The injection device 1 comprises one or more sensors 41, 42, shown in FIG. 2, for detecting the puncturing depth that was set. In the exemplary embodiment shown, the setting facility comprises a first manually-actuated setting element 10, the actuation of which allows a user to set the puncturing depth of the first motion profile, and a second manually-actuated setting element 1, the actuation of which allows a user to set the puncturing depth of the second motion profile. The first setting element 10 is a setting wheel that can be rotated to set the first puncturing depth for the injection of insulin. The second setting element 11 is a screwed-on front cap that can be rotated with respect to a cylindrical device housing 12, whereby the distance of the front cap 11 and thus the distance of a device opening 19 from the cylindrical device housing 12 is changed by rotating the front cap.

In order to generate a puncturing wound, the front cap of the injection device 1 is pressed to a body part. In a puncturing process, the injection needle 4 emanates from the device opening 19 and into the body part pressed to the device 1. It is obviously also feasible to provide the device opening 19 such that tissue of a body part pressed to it bulges into the front cap such that a puncturing wound can be generated without the injection needle 4 having to emanate from the interior of the device.

It should be noted that in embodiments of the invention, the setting facility 10, 11 may comprise separate manually actuated setting elements 10, 11. However, it has been found that the operability of an injection device 1, in which a first setting element 10 serves for setting a puncturing depth of the first device function and a second setting element 11 serves for setting the puncturing depth of a second device function, is significantly better since it is intuitively clear to users which of the two puncturing depths is changed by actuating the corresponding setting element and thus the risk of incorrect operation may be reduced.

A display facility 26, 27 for displaying the set puncturing depth belongs to the setting facility 10, 11 of the exemplary embodiment shown. In this context, it is useful for the display facility to allow for the simultaneous display of a set first puncturing depth of the first motion profile and a set second puncturing depth of the second motion profile. This is provided in the exemplary embodiment shown in that the rotatable setting elements 10, 11 are provided with markings that act in conjunction with markings 26, 27 provided on the housing 12 that are fixed with respect to rotations and thus allow the set puncturing depths to be read. The setting wheel in the setting element 10 is provided with numbers that act in conjunction with the marking 26 which may be any suitable shape, such as the form of a triangle or arrow, for example. The marking 26 may be arranged on the housing 12. A user may recognize to which of the numbers the triangle 26 arranged on the housing 12 points and deduce the set puncturing depth of the first motion profile therefrom. In the second setting element, a corresponding triangle can be rotated with respect to the housing 12, while a sequence of numbers is provided on the housing and forms the display facility 27. As before, a user may recognize to which of the numbers the triangle points and thus deduce the set puncturing depth of the second motion profile in the setting element 11 also.

Moreover, the injection device 1 shown has an activation facility that can be used to optionally trigger a motion of the injection needle 4 with the first motion profile or second motion profile. In the exemplary embodiment shown, the activation facility comprises a first manually-actuated trigger element 13, the actuation of which allows a user to initiate a motion of the injection needle with the first motion profile, and a second manually-actuated trigger element 14, the actuation of which allows a user to trigger a motion of the injection needle 4 with the second motion profile. The trigger elements 13, 14 are provided in the form of buttons in the exemplary embodiment shown. The use of separate trigger elements 13, 14 for the two device functions renders it easier for the user to activate the device function desired in the individual case. However, a single manually-actuated trigger element may be sufficient as long as it is feasible to select by means of other measures which of the two device functions is activated by actuating the trigger element.

The injection device 1 shown has a dosing facility 15 for setting the quantity of agent to be pressed out from an inserted insulin vial 3 during an injection process. The dosing facility 15 has a manually-actuated setting wheel, whose position, and thus the set quantity of insulin, is displayed through an inspection window of the housing 12. The filling status of an inserted insulin vial can be inspected visually since the housing 12 is transparent in the area of the insulin compartment 2 such that a user can easily see how much insulin is still present in an inserted vial 3.

The injection device 1 shown has an integrated measuring unit 17 for assaying a body fluid sample that can be obtained by means of a puncturing wound of the injection needle 4 according to the second motion profile. In the exemplary embodiment shown, the measuring unit 17 is suitably fitted for the determination of the glucose content of a body fluid sample through the use of suitable commercial test strips.

A slit 18 is arranged in the housing 12 of the injection device 1, whereby a test element, for example in the form of a suitable test strip, that was wetted with a body fluid sample can be inserted in the slit 18 for measuring the glucose concentration. From wetting the test element with body fluid results a change of color of the test element whose intensity depends on the glucose concentration of the body fluid sample. The degree of color change can be determined photometrically by means of the measuring unit 17. In embodiments, measuring unit 17 can also be an electrochemical measuring unit, or other suitable type of measuring device.

The measuring unit 17 is connected to a central analytical and control unit 21 that is attached to a display facility 20 in the form of a liquid crystal display and can be used to display a glucose content that has been determined. In one embodiment, analytical and control unit 21 is provided in the form of an ASIC (application-specific integrated circuit) that is arranged jointly with a memory 22 on a circuit board. The measuring unit 17 is actuated by means of the operating element 24. As a liquid crystal display with segmental display, the display facility 20 can be used to display device information in addition to displaying measuring results. It should be noted that display facility 20 may be any suitable display.

The analytical and control unit 21 is connected to an interface 25 via which data can be exchanged with external systems, for example a PC or an insulin pump. The interface 25 can be provided in the form of a cable-based serial interface or infrared interface. Also feasible is an RF interface and more complex interfaces according to Bluetooth or WLAN. For the device 1 to be operable without having to be connected to mains voltage it may contain a power source, for example in the form of batteries or solar cells.

Data concerning the quantity of insulin injected in an injection process, for example, can be output via the interface 25. For this purpose, the injection device 1 comprises a sensor 40 for detecting the injected quantity that is shown in FIG. 2. The sensor 40 is connected to the analytical and control unit 21 and converts a mechanical motion of the dosing facility 15 to electrical signals in the exemplary embodiment shown. The dosing facility 15 comprises a manually-actuated setting wheel, whereby the rotation motion of the wheel is measured using the sensor 40 such that the actual device setting regarding the quantity of insulin to be injected can be determined by analysis of the signals 40.

A central analytical and control unit 21 of the injection device 1, may also be employed in an embodiment lacking an integrated measuring unit 17. An injection device 1 lacking an integrated measuring unit 17 can, for example, be part of a system that includes a separate measuring device for determining an analyte concentration of a body fluid, in particular the glucose concentration, as a further component of the system. The central analytical and control unit 21 of the injection device 1 can, for example, be provided in the form of a microprocessor and communicate with the separate measuring device via the interface 25. By this means, the analytical and control unit 21 of the injection device 1 can be used for storage and analysis of all data that is relevant for treatment. For example, puncturing depth settings, injection dosages, and injection times as well as analyte concentration values can be stored. As a supplement, additional patient data, for example data concerning food intake and physical exercise, can be analyzed and stored by the analytical and control unit 21 of the injection device 1. The injection device 1 can receive patient data of this type from a further component of the system, for example a personal data assistant or a separate measuring device with input facility, for example, via the interface 25.

As mentioned earlier, for detection of the set puncturing depths, the injection device 1 comprises sensors 41, 42 that are also attached to the analytical and control unit 21. The sensors 41, 42 measure a mechanical motion of the setting facility 10, 11 and, in operation, convert it to electrical signals from which the set puncturing depth can be determined. The device settings made manually and detected by means of the sensors 40, 41, 42, which are effected in the exemplary embodiment shown by means of rotational motions, for example of the setting elements 10, 11 or of the setting wheel of the dosing facility 15, are stored by the analytical and control unit 21 and can be transmitted via the interface 25.

The drive of the injection device shown in FIG. 1 may be a spring drive. Spring drives for injection devices and puncturing devices are used to generate puncturing wounds for obtaining body fluid samples for diagnostic purposes, and they are known, for example, from EP 0565970 B1, U.S. Pat. No. 5,318,589 and U.S. Pat. No. RE 35,803, each of which is expressly incorporated by reference herein in its entirety. For this reason, we refrain from presenting here a graphical depiction and more detailed description of construction details of the spring drive.

In the exemplary embodiment shown, the injection needle 4 is moved in concert with the insulin vial 3 by the drive during a puncturing motion. In this process, the insulin vial is carried by a sled 30 that is mobile in the direction of puncturing and moved by the drive. In order to minimize friction, the sled 30 is borne on guiding elements, preferably on tracks, such that it can be made to travel. In the exemplary embodiment shown in FIG. 3, the sled 30 is made to travel in the direction of puncturing jointly with the insulin vial 3 and the injection needle 4 both in the first device function and in the second device function. For a puncturing motion, though, it is basically sufficient to move the injection needle 4, whereby the insulin vial 3 can remain unmoved with respect to the housing 12.

Figure 4:
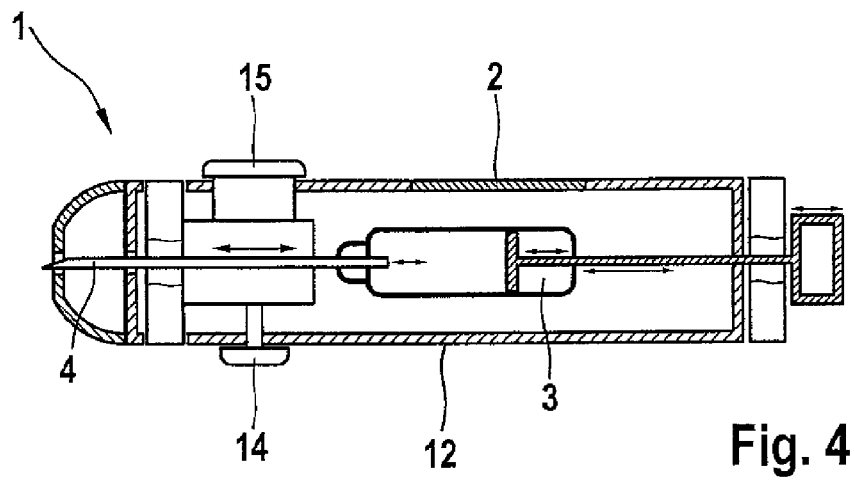
FIG. 4 shows a schematic cross-sectional view of another exemplary embodiment of an injection device according to the invention.

An exemplary embodiment of an injection device of this type is shown in FIG. 4. It is particularly useful to combine these two drive options, i.e. to move the puncturing needle 4 jointly with the insulin vial 3 in one of the two device functions and to move the injection needle 4 with respect to the insulin vial 3, which can remain fixed in place with respect to the housing 12, in the other device function. By this means, the separation of the motion mechanisms allows the two puncturing depths for the first and the second motion profile to be set independent of each other and the two motion profiles to be activated independent of each other in a particularly simple fashion. In this context, it is particularly useful to move the injection needle 4 jointly with the vial 3 in the second motion profile, since this facilitates a particularly rapid puncturing and returning motion, and to move the injection needle 4 with respect to the vial 3 in the first motion profile.

In order to generate a puncturing wound, the front face of the injection device 1 gets pressed to a body part of the user. The injection device 1 has a removable front cap 31 at its front face, which front cap 31 is provided with an opening 19 through which the injection needle 4 can move out during a puncture.

Figures 5, 6, 7:
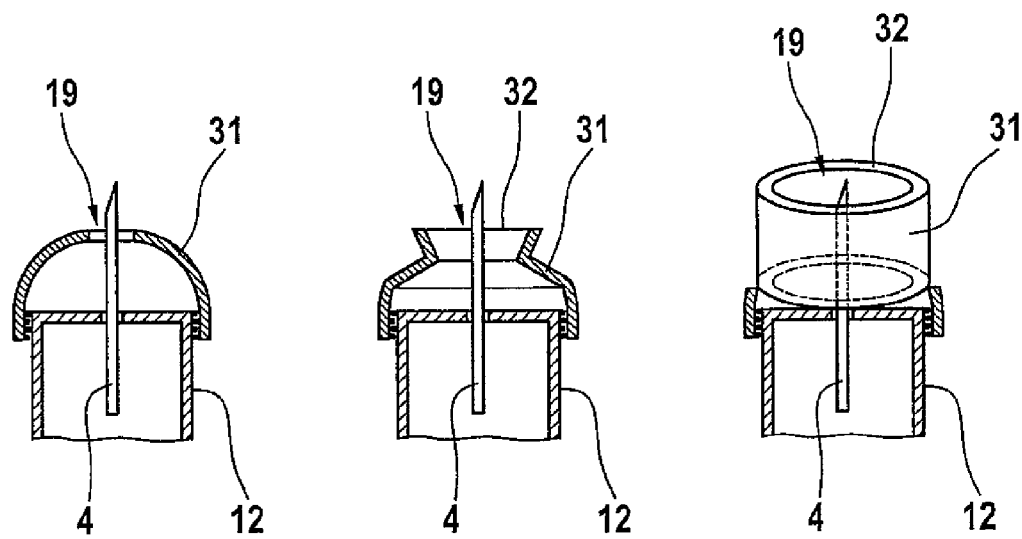
FIG. 5 shows a detail view of the front cap of the exemplary embodiments shown in FIGS. 1 and 4.
FIG. 6 shows another exemplary embodiment of a front cap.
FIG. 7 shows another exemplary embodiment of a front cap.

FIGS. 5 to 7 show various exemplary embodiments of suitable front caps 31. In particular, in the exemplary embodiment shown in FIG. 6, the opening 19 is sufficiently large for a finger tip that is pressed to the opening 19 to bulge into the opening 19 and, accordingly, the injection needle 4 does not necessarily have to move out from the interior in order to generate a puncturing wound. In order to obtain a sufficient body fluid sample for diagnostic purposes with the second device function even at minimal puncturing depth, it is useful for the front cap 31 at the device opening 19 to comprise a funnel-shaped press-against surface 32 that conforms to a finger tip pressed to it and promotes the supply of blood to it. By this means, a sufficiently large sample of body fluid can be obtained more easily because of the improved supply of blood.

For the first device function that is used to inject insulin, the front cap 31 can be removed in order to minimize the bleeding of a puncturing wound generated for the injection of insulin. The front caps 31 are preferably attached by being screwed onto the device housing 12. A suitable sensor can be used to determine whether or not a front cap 31 is attached to the housing 12. The analytical and control unit 21 (FIG. 2) can use the sensor result to block the first or the second device function such that only the second device function can be activated when the front cap 31 is attached, and only the first device function can be activated when the front cap 31 is missing.

While the invention has been taught with specific reference to these embodiments, one skilled in the art will recognize that changes can be made in form and detail without departing from the spirit and scope of the invention. The described embodiments are to be considered, therefore, in all respects only as illustrative and not restrictive. As such, the scope of the invention is indicated by the following claims rather than by the description.

The invention claimed is:

1. An injection device for the injection into a patient of a medical agent contained within a vial, comprising:
   a housing;
   a compartment configured to receive the vial;
   a needle that is movable in a first direction in order to puncture the patient; and
   a pressing member configured to force the medical agent from the vial and through the needle into the patient;
   wherein the needle is movable from an initial position in accordance with a first motion profile in which the needle moves a first distance relative to the housing followed by a rest period, and in accordance with a second motion profile in which the needle is returned to the initial position without a rest period after moving relative to the housing to puncture the patient.

2. The injection device as set forth in claim 1 further including an activation mechanism capable of initiating motion of the needle in accordance with the first motion profile or the second motion profile.

3. The injection device as set forth in claim 2 wherein the activation mechanism includes a first trigger element causing motion of the needle in accordance with the first motion profile.

4. The injection device as set forth in claim 3 wherein the activation mechanism includes a second trigger element causing motion of the needle in accordance with the second motion profile.

5. The injection device as set forth in claim 2 further including a mechanism for setting a first puncturing depth for the first motion profile and a second puncturing depth for the second motion profile.

6. The injection device as set forth in claim 5 further including a display capable of displaying the first puncturing depth and the second puncturing depth.

7. The injection device as set forth in claim 5 wherein the activation mechanism includes a first setting element for setting the first puncturing depth and a second setting element for setting the second puncturing depth.

8. The injection device as set forth in claim 1 further including a measuring unit for assaying a body fluid sample.

9. The injection device as set forth in claim 8 wherein the measuring unit is a blood glucose meter.

10. The injection device as set forth in claim 1 further including a cap connected to the housing.

11. The injection device as set forth in claim 10 wherein the cap includes an opening and the needle extends through the opening during puncturing.

12. The injection device as set forth in claim 1 wherein the needle moves with respect to the vial when the needle moves in accordance with the first motion profile.

13. The injection device as set forth in claim 1 wherein the needle and the vial move with respect to the housing in accordance with the second motion profile.

14. The injection device as set forth in claim 1 wherein the needle moves with respect to the vial when the needle moves in accordance with one of the motion profiles, and the needle and the vial move with respect to the housing in accordance with the other of the motion profiles.

15. The injection device as set forth in claim 1 further including a sensor for detecting at least one of a first puncturing depth or a second puncturing depth.

16. The injection device as set forth in claim 1 wherein the pressing member forces the medical agent from the vial and through the needle during the rest period.

17. An injection device for the injection into a patient of a medical agent contained within a vial comprising:
   a housing including a compartment configured to receive the vial;
   a needle that may be moved in a first direction in order to puncture the patient;
   a pressing member configured to force the medical agent from the vial; and
   advancement mechanics for moving the needle;
   wherein the advancement mechanics effect in a first device function for an injection process a first motion profile of the needle in which a resting phase follows after an advancement motion of the needle relative to the housing, during which resting phase the needle is at rest with respect to the housing for the injection process; and wherein the advancement mechanics effect in a second device function for obtaining a body fluid sample for diagnostic purposes a second motion profile of the needle in which a returning motion follows immediately after a puncturing motion.

18. The injection device as set forth in claim 17 further including a cap connected to the housing.

19. The injection device as set forth in claim 18 wherein the cap includes an opening and an arcuate cross section.

20. The injection device as set forth in claim 18 wherein the cap has a substantially cylindrical shape.

21. The injection device as set forth in claim 18 wherein the cap includes a portion having the cross-sectional shape of a frustum.

22. The injection device as set forth in claim 17 wherein the needle moves with respect to the vial when the needle moves according to the second motion profile.

23. The injection device as set forth in claim 17 further including a measuring unit capable of assaying a body fluid sample.

24. The injection device as set forth in claim 23 wherein the measuring unit is a blood glucose meter.

25. The injection device as set forth in claim 23 wherein the measuring unit is a photometrical unit.

26. The injection device as set forth in claim 23 wherein the measuring unit is an electrochemical unit.

27. The injection device as set forth in claim 17 further including a trigger element capable of actuating movement of the needle in accordance with one of the first motion profile or the second motion profile.

28. The injection device as set forth in claim 27 further including a second trigger element capable of actuating movement of the needle in accordance with the other of the first motion profile or the second motion profile.

29. The injection device as set forth in claim 17 further including a first setting element capable of setting a puncture depth of the needle in accordance with movement of the needle based upon the first motion profile.

30. The injection device as set forth in claim 29 further including a second setting element capable of setting a second puncture depth of the needle in accordance with movement of the needle based upon the second motion profile.

31. The injection device as set forth in claim 29 further including a display capable of displaying the first puncture depth or the second puncture depth.

32. The injection device as set forth in claim 31 wherein the display is a liquid crystal display.

* * * * *